United States Patent [19]

Lundy

[11] Patent Number: 5,282,789
[45] Date of Patent: Feb. 1, 1994

[54] DISPOSABLE MEDICINE APPLICATOR

[75] Inventor: William A. Lundy, Statesville, N.C.

[73] Assignee: Niemand Industries, Inc., Statesville, N.C.

[21] Appl. No.: 947,291

[22] Filed: Sep. 15, 1992

[51] Int. Cl.$^5$ .................................. A61M 31/00
[52] U.S. Cl. ......................... 604/55; 604/59; 604/218; 604/15; 604/48; 206/363; 206/364; 222/41; 222/49; 222/386; 141/26
[58] Field of Search ............. 604/11, 15, 16, 38, 604/48, 54, 55, 59, 60, 111, 187, 218, 220, 207, 208, 197; 206/363, 364, 438; 128/838, 840; 222/41, 49, 386; 141/25, 26, 114

[56] References Cited

U.S. PATENT DOCUMENTS

| | | |
|---|---|---|
| 306,620 | 10/1984 | Jaeger . |
| 1,960,858 | 5/1934 | Strauch .................. 604/191 X |
| 2,060,513 | 11/1936 | Marx . |
| 2,077,176 | 4/1939 | Lermer .................. 604/220 |
| 2,195,675 | 4/1940 | Lewis .................... 604/218 |
| 2,355,917 | 8/1944 | Knight ................... 604/11 |
| 2,486,056 | 10/1949 | Oclassen . |
| 2,516,846 | 8/1950 | Betz ...................... 604/59 |
| 2,538,197 | 1/1951 | Holtman . |
| 2,680,442 | 6/1954 | Linzmayer ............. 604/197 X |
| 2,691,982 | 10/1954 | Jones et al. . |
| 2,709,436 | 5/1955 | Lynn ..................... 206/363 X |
| 2,711,173 | 6/1955 | Seidler . |
| 2,712,315 | 7/1955 | Rice ..................... 206/363 X |
| 2,720,881 | 10/1955 | Jones . |
| 2,724,385 | 11/1955 | Lockhart ............... 206/364 X |
| 2,747,574 | 5/1956 | Lorenzo ................. 604/59 |
| 2,879,770 | 3/1959 | Graham, Jr. . |
| 3,356,281 | 12/1967 | Buttery . |
| 3,642,000 | 2/1972 | Baker .................... 604/218 |
| 3,869,062 | 3/1975 | Jaeschke et al. . |
| 4,573,964 | 3/1986 | Huffman ................. 604/15 |

FOREIGN PATENT DOCUMENTS

| | | | |
|---|---|---|---|
| 473134 | 4/1951 | Canada ................ 604/15 |
| 1454966 | 11/1976 | United Kingdom ..... 222/49 |

OTHER PUBLICATIONS

Page from Niemand Industries, Inc. Advertising Brochure.

Primary Examiner—John D. Yasko
Assistant Examiner—Mark O. Polutta
Attorney, Agent, or Firm—Bell, Seltzer, Park & Gibson

[57] ABSTRACT

A disposable applicator for introducing medicine into a body cavity is disclosed including a barrel and a plunger slidably positioned within the barrel. The barrel and plunger are preferably formed of a plurality of spirally wound paper layers. The plunger includes first and second opposing ends. The first end of the plunger is completely closed and serves as the working surface of the plunger. The second end of the plunger is substantially closed by inwardly crimped portions to prevent the accidental or inadvertent filling of the hollow plunger with a gel-like medicine rather than the barrel. A predetermined number of applicators, such as seven, are preferably packaged within a tubular container.

15 Claims, 1 Drawing Sheet

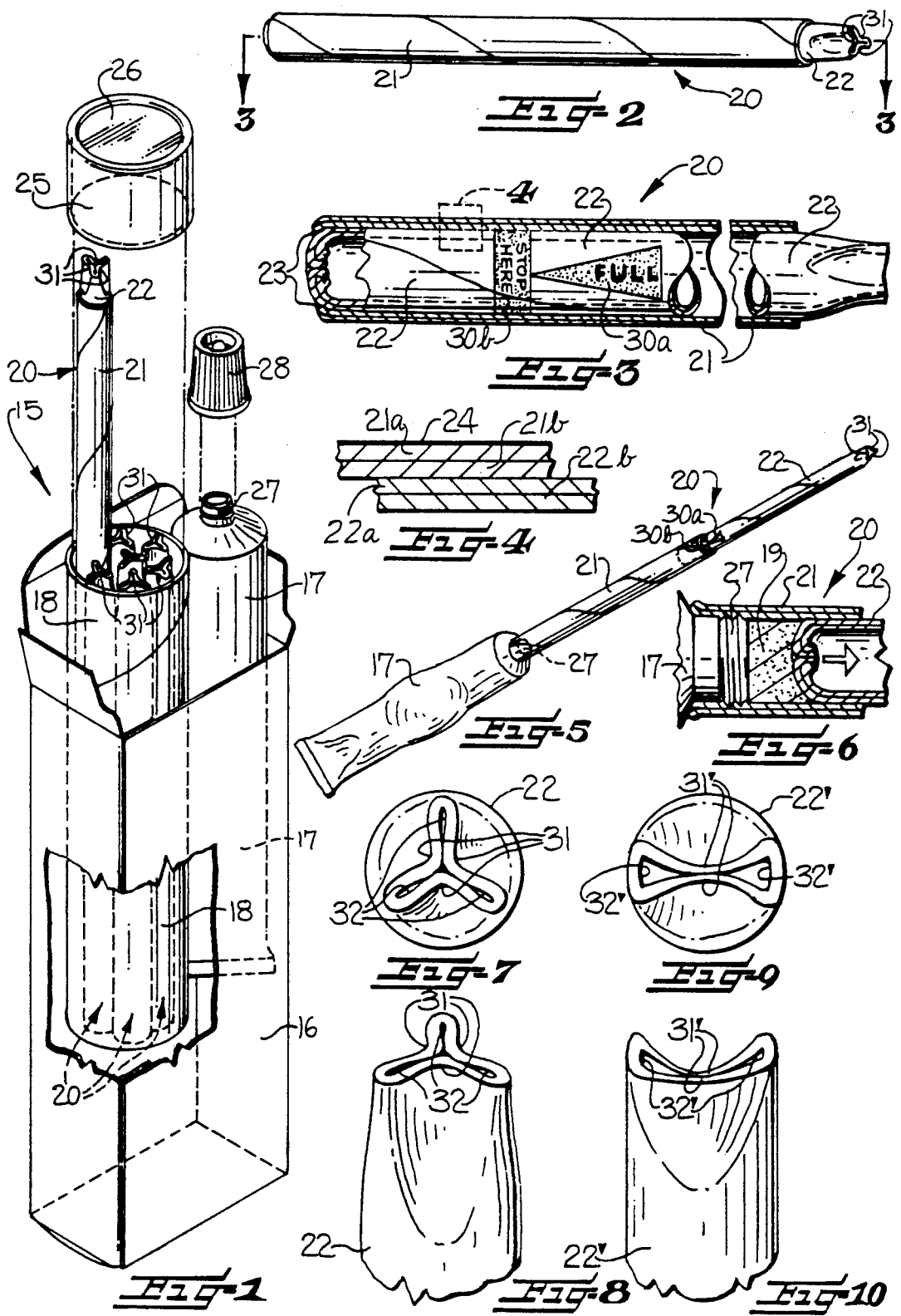

DISPOSABLE MEDICINE APPLICATOR

FIELD OF THE INVENTION

The present invention relates to the field of applicators for introducing a medicine into a cavity of the body, and more particularly, to a disposable applicator for introducing a medicine into the body, such as for treating vaginal yeast infections and the like.

BACKGROUND OF THE INVENTION

Disposable or single use applicators are known for facilitating the injection of a medicine into a body cavity, such as for treating vaginal yeast infections and the like. For example, U.S. Pat. No. 2,691,982 and U.S. Pat. No. 2,720,881, both to Jones, each discloses a disposable applicator including a barrel with a quantity of medicine stored in a rupturable container positioned within one end of the barrel. A tubular plunger having a star-shaped working end is pushed into the barrel to rupture a seal on the end of the container and then progressively crush the medicine bearing container to thereby eject the medicine from the end of the barrel. Another similar applicator including a self-contained dosage of medicine is disclosed in U.S. Pat. No. 2,486,056 to Oclassen.

Modern applicators are currently available for treating vaginal yeast infections and the like, typically for a seven day treatment period during which daily doses of the medicine are administered. One such medicine for treating vaginal yeast infections is available from Ortho Pharmaceutical Corporation of Raritan, N.J. under the trademark designation Terazol®7. Such medicines are commonly supplied in a seven day treatment package including a squeeze tube along with a single reusable plastic applicator. The squeeze tube contains a seven day supply of the gel-like medicine. The applicator supplied as part of the treatment package includes a plastic barrel and an inner sliding plastic plunger for ejecting the medicine from the barrel.

Unfortunately, a single plastic applicator must be cleaned for reuse during the seven day treatment period. The medicines used are not typically readily soluble in water and, therefore, cleaning of a used applicator is often difficult and messy. Moreover, if cleaning of the plastic applicator is not correctly performed, the patient has a significantly greater chance of reinfection. Accordingly, one approach has been to provide seven plastic applicators within the overall treatment package so that reuse of a single applicator is not required. Unfortunately, such disposable plastic applicators are not environmentally friendly, that is, they are not biodegradable. Another shortcoming of plastic applicators is that they cannot typically receive printing inks thereon for advertising or instructional purposes.

The assignee of the present invention, Niemand Industries, Inc., had developed a spirally wound paper applicator for vaginal yeast infections and the like that was disposable, readily biodegradable, and capable of being printed on, thus overcoming several of the disadvantages of other applicators. The applicator included a paper barrel having opposing open ends and a slidable plunger having a closed end for dispensing or ejecting medicine out of the barrel. The applicator included an inturned lip of the end of the barrel inserted into the patient, the paper was approved for direct human contact, and indicia on the plunger indicated when the plunger was filled to the desired dosage. Niemand's disposable applicators were distributed to doctors for use with medicine samples as typically provided to doctors by pharmaceutical companies.

The plunger of the disposable applicator offered by Niemand had an open end extending from the barrel, and the barrel itself had an open opposite end. Thus, the applicator presented two open ends of similar diameter to the patient for filling with the medicine from a squeeze tube. Accordingly, many patients inadvertently or accidentally filled the hollow tubular plunger rather than the barrel, despite printed indicia on the end of the plunger instructing the patient to "FILL OTHER END" of the applicator. Once the hollow tubular plunger is inadvertently filled with medicine, the quantity of medicine is wasted and the applicator is typically discarded. The lost amount of medication may significantly reduce the effectiveness of the overall treatment.

In addition to the shortcoming with respect to incorrect filling of the disposable applicator, the previous applicator offered by Niemand was delivered to physicians in large lots of individual applicators. Accordingly, the physician was required to separate out a desired number of applicators for a given number of treatments, such as typically seven, and give the medicine and applicators to the patient either as individual items, in a bag, or in another makeshift package. Thus, individual applicators could be readily misplaced and the full prescribed treatment period not followed by the patient.

SUMMARY OF THE INVENTION

In view of the foregoing background, it is therefore an object of the invention to provide a medicine applicator that is disposable and biodegradable, and that cannot be inadvertently filled at the wrong end thereby wasting a quantity of the medicine, reducing the effectiveness of the overall treatment, and rendering the applicator unusable.

It is another object of the invention to provide a package for containing a desired number of disposable applicators corresponding to a desired number of treatments for a particular medicine so that the patient may readily follow the required treatment schedule.

These and other objects, advantages, and features of the invention are provided by a disposable applicator including a tubular barrel and a tubular plunger slidably positioned within the barrel wherein the plunger has a first closed end to serve as the working end of the plunger and a second opposite end that is substantially closed to prevent inadvertent or accidental filling of the hollow plunger with medicine rather than correctly filling the barrel. Both the barrel and the plunger are formed of a plurality of spirally wound paper layers, the paper being biodegradable and also preferably of a type approved for direct human contact.

The barrel has opposing first and second open ends with the first open end for permitting the passage of the gel-like medicine therethrough to fill the barrel and for being inserted into the body cavity thereby permitting the subsequent ejection of the medicine from the thus filled barrel. The gel-like medicine is typically input into the barrel from a squeeze tube which is temporarily coupled to the first end of the barrel.

The plunger of the disposable applicator is movable relative to the barrel between an unfilled position wherein the barrel contains no medicine and a filled position wherein the barrel contains the desired dosage of medicine. Preferably the plunger has a length greater than the length of the barrel so that a predetermined length of the plunger extends outwardly from the second end of the barrel when the plunger is in the unfilled position. The substantially closed end of the plunger preferably includes inwardly crimped portions of the plunger. These inwardly crimped portions may extend lengthwise along part or all of the predetermined length of the plunger that extends outwardly from the second end of the barrel when the plunger is in the unfilled position.

The inwardly crimped portions of the plunger and adjacent portions of the plunger are preferably contained within an imaginary circle defined by the outer surface of the plunger. Thus, a plurality of applicators can be readily packaged in side-by-side relation. In one embodiment of the invention, lengthwise extending inwardly crimped portions of the plunger define a star pattern in end view such as having three or more radial points. In another embodiment of the invention, lengthwise extending inwardly crimped portions of the plunger define a saddle pattern in end view. As would be readily appreciated by those skilled in the art, other configurations and modifications to the plunger end to substantially close the end may also be used to prevent the inadvertent or accidental filling of the hollow plunger rather than the barrel of the applicator.

The first open end of the barrel preferably has an inturned lip to serve as a smooth or finished surface for insertion into a body cavity. The inturned lip also receives the first end of the plunge thereagainst when the plunger is in the unfilled position to thereby serve as a stop to prevent the plunger from extending outwardly beyond the first open end of the barrel, such as during shipping or handling of the applicator. The plunger also preferably includes printed indicia means on a predetermined outer surface portion thereof for indicating that the barrel contains the desired dosage of medicine as occurs during filling of the barrel. The indicia on the barrel is exposed as the plunger is moved progressively outwardly from the barrel and reaches the filled position.

Another aspect of the present invention is the packaging of a predetermined number of disposable applicators, as described above, within a container to thereby facilitate treatment with a desired number of periodic dosages of the medicine. Typically the container is packaged together with a squeeze tube of medicine. The container preferably has a tubular shape with opposing first and second ends, the first end of the container being closed and the second end of said container being open and covered by a removable closure cap. A predetermined number of disposable applicators, typically seven for treating vaginal yeast infections, are positioned within the container corresponding to the number of desired dosages of medicine for the treatment period. Like the barrel and plunger of the disposable applicator, the container is preferably formed of a plurality of spirally wound paper layers for biodegradability.

The length of each applicator is preferably substantially the same as the interior length of the container to prevent unwanted lengthwise movement of the applicators within the container, such as during shipping. Similarly, the interior cross-sectional diameter of the container is substantially equal to three times the diameter of the applicators so that seven applicators will fit compactly within the container and will have limited radial movement within the container to prevent damage, such as during shipping.

BRIEF DESCRIPTION OF THE DRAWINGS

FIG. 1 is an exploded perspective view of an overall package including a container having seven disposable applicators according to the invention and a squeeze tube of medicine for use with the applicators.

FIG. 2 is a side elevational view of a disposable applicator as shown in FIG. 1.

FIG. 3 is a view, partially in section, of the disposable applicator taken along lines 3—3 of FIG. 2.

FIG. 4 is a greatly enlarged cross-sectional view of a portion of the disposable applicator within box 4 of FIG. 3.

FIG. 5 is a perspective view of the disposable applicator according to the invention in the filled position and coupled to the medicine squeeze tube from which the applicator has been filled.

FIG. 6 is greatly enlarged cross-sectional view of the coupling of the disposable applicator and the squeeze tube as shown in FIG. 5.

FIG. 7 is an end view of a first embodiment of an end of the plunger of the disposable applicator according to the invention.

FIG. 8 is a perspective view of the first embodiment of the plunger of the disposable applicator shown in FIG. 7.

FIG. 9 is an end view of a second embodiment of an end of the plunger of the disposable applicator according to the invention.

FIG. 10 is a perspective view of the second embodiment of the plunger of the disposable applicator shown in FIG. 9.

DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, applicant provides these embodiments so that this disclosure will be thorough and complete, and will fully convey the scope of the invention to those skilled in the art. Like numbers refer to like elements throughout and prime notation is used to indicate similar elements in alternate embodiments. The thickness of layers are exaggerated for clarity.

Referring to FIG. 1, a treatment kit 15 for vaginal yeast infections and the like is shown. The kit 15 includes an overall generally rectangular box 16 enclosing a medicine squeeze tube 17 and a container 18 for a plurality of disposable applicators 20 according to the invention. The container 18 includes a removable closure cap 25 With a transparent window portion 26 at the top end thereof. The bottom of the container is preferably closed by a paper disk, not shown. A paper disk may also alternately be used in place of the transparent window. The squeeze tube 17 includes a threaded end 27 onto which may be secured a twist-off cap 28.

The number of disposable applicators 20, seven in the illustrated embodiment, corresponds to the desired number of treatments for a particular medicine. For typical over-the-counter or prescription treatments for vaginal yeast infections, a daily dose of a gel-like medicine is given for seven successive days. Such a medicine is disclosed in U.S. Pat. No. 4,358,449 and is sold under the trademark Terazol®7 by Ortho Pharmaceutical Corporation of Raritan, N.J. As would be readily understood by those skilled in the art, other treatment periods are possible, and even a single treatment requiring only a single disposable applicator may be used for certain medicines.

Since each disposable applicator 20 according to the invention is used only once before being discarded, the problems associated with cleaning reusable plastic applicators are overcome. In addition, the likelihood of reinfection is greatly reduced when using the disposable applicator 20 according to the present invention compared to reusing plastic applicators.

Referring now additionally to FIGS. 2–6, the disposable applicator 20 according to the invention is best understood. The applicator 20 includes a barrel 21 having a tubular shape and a plunger 22 also having a tubular shape slidably positioned within the barrel. The plunger 22 is movable relative to the barrel between an unfilled position (FIG. 3) and a filled position (FIG. 5).

The barrel 21 and the plunger 22 are both formed of a plurality of spirally wound paper layers 21a, 21b; 22a, 22b. The barrel's outermost paper layer 21a may include a wax coating 24 thereon as shown in the greatly enlarged view of FIG. 4. The paper is preferably biodegradable and is also preferably of a type approved for direct human contact, such as paper manufactured by Eastern Fine Papers of Brewer, Me. and available under the description white special sulphite. The adhesive used to secure the adjacent paper layers together is also preferably of a type approved for direct human contact. The paper of the plunger 22 or the barrel 21 may readily receive printing inks thereon for instructional or advertising purposes.

The barrel 21 has first and second opposing open ends wherein the first end is adapted to permit passage of the medicine from the squeeze tube 17 into the interior of the tube (FIGS. 5 and 6) during filling. The first end of the barrel 21 is inserted into the desired body cavity of the patient. When the plunger 22 is moved from a filled position to the unfilled position by the patient or a doctor, the medicine is ejected out of the first end of the barrel 21 into the body cavity.

To fill the applicator 20, the first end of the barrel is either pushed or rotated onto the threaded end 27 of the squeeze tube 17. The paper of the barrel 21 is sufficiently pliable and the opening of the first end of the barrel sized to form a seal between the squeeze tube and the barrel after the threaded end of the squeeze tube is inserted into the barrel as best shown in FIGS. 5 and 6. Squeezing the squeeze tube 17, forces the medicine 19 to fill the interior of the barrel 21 (FIG. 6) and causes the plunger 22 to extend progressively outwardly from the second end of the barrel 21 (FIG. 5).

The plunger 22 has opposing first and second ends—the first end being completely closed to serve as the working surface of the plunger. The closed end may be formed by upsetting the paper layers at the first end of the plunger 22 and folding the layers inwardly and compressing the layers to thereby form the closed end. Typically an elongate mandrel (not shown) is first inserted into the tubular plunger 22 to support same as the end portion is folded and compressed.

The first end of the barrel 21 also preferably includes an inturned lip 23 which presents a smooth and finished surface for insertion into a body cavity. The inturned lip 23 also serves as a stop for the closed end of the plunger 22 as best shown in FIG. 3. The inturned lip 23 prevents the plunger 22 from sliding out of the first end of the barrel, such as during shipping or handling prior to use.

As shown best in FIG. 2, the plunger 22 has a predetermined length slightly larger than the length of the barrel 21. For treating vaginal yeast infections, for example, the barrel 21 may be about 4 and ⅜" long and ⅝" in diameter, while the plunger 22 is about 5 and ¼" long. Thus a predetermined length of the plunger 22, about ½" for the typical dimensions given, extends outwardly from the second end of the barrel 21. This extra length serves to insure that the full dosage of medicine 19 contained within the filled barrel 21 is injected into the body cavity of the patient. During injection of the medicine 19 into a body cavity, the second end of the plunger 22 will be pushed flush with the second end of the barrel 21 causing the first end of the plunger to protrude outwardly from the first end of the barrel, thereby ensuring that the barrel is completely emptied.

FIGS. 3 and 5 illustrate another feature of the applicator wherein printed indicia 30a, 30b are provided on predetermined outer surface portions of the plunger 22. The indicia is readily printed on the outer paper layer of the plunger, in contrast to prior art plastic applicators wherein printing is typically not possible. As would be readily understood by those skilled in the art, the ink used for the indicia 30a, 30b is preferably of a type suitable for direct human contact. As shown in the illustrated embodiment, as the barrel 21 is filled, the plunger 22 is pushed out of the barrel. The arrow-shaped indicia 30a with the word "FULL" is progressively exposed as the barrel is filled. If the patient continues to fill the barrel, the band indicia 30b with the phrase "STOP HERE" is exposed. Thus the patient has clear and simple instructions for filling the barrel 21 with the correct dosage of medicine 19.

The disposable applicator 20 according to the present invention includes a plunger 22 having a second end which is substantially closed to prevent the inadvertent or accidental coupling of the squeeze tube 17 to this end of the plunger. In the prior art, a disposable applicator included a plunger having an open second end thereby presenting the patient with a tubular applicator having opposing open ends of approximately the same diameter, one being the barrel and the other being the open end of the plunger. The patient did not always read or appreciate the indicia indicating that the end opposite the exposed plunger end was to be filled. Thus, patients incorrectly filled the hollow plunger rather than the barrel. Filling the plunger rather than the barrel wasted the quantity of medicine, reduced the effectiveness of the overall treatment program, and also typically rendered the applicator unusable. The applicator 20 according to the present invention overcomes this significant shortcoming of the prior art in a straightforward and cost effective manner by providing a substantially closed second end for the plunger 22.

Referring now to FIGS. 7–10, two embodiments of the substantially closed end of the plunger 22 will be described. As shown in FIGS. 7 and 8, one embodiment includes three inwardly crimped lengthwise extending portions 31 of the plunger defining a star pattern having three radial points in end view. As would be readily understood by those skilled in the art, the star pattern may include three or more radial points. As illustrated, gaps 32 are formed between adjacent folds.

Preferably the inwardly crimped portions 31 of the plunger 22 and adjacent portions of the plunger are contained within the imaginary circle defined by the outer surface portion of the plunger which preferably has a circular cross-section. Accordingly, a group of the applicators 20 may be compactly packaged together in a cylindrical arrangement (FIG. 1). In addition, the inwardly crimped portions 31 preferably extend along only a portion of the predetermined length of the plunger 22 which extends outwardly from the barrel 21 when the plunger is in the unfilled position (FIG. 2).

A second embodiment of the substantially closed end of the plunger 22' is shown in FIGS. 9 and 10. Two spaced apart lengthwise extending crimped portions 31' define a saddle pattern in end view. Gaps 32' are left between adjacent folds. As would be readily understood by those skilled in the art, the inwardly crimped portions 31, 31' of both illustrated embodiments may be compressed to leave no gaps. Other modifications and configurations to the second plunger end may also be made so long as the end is substantially closed to prevent inadvertent or accidental filling thereof. It has been found according to the invention that crimping is a preferred method for substantially closing the end because no mandrel need be temporarily inserted into the interior of the plunger 22 as, for example, when forming the completely closed first end of the plunger (FIG. 3).

Referring again to FIG. 1, another aspect of the present invention is the combination of a predetermined number of the disposable applicators 20 as described above and a container 18 therefor. Preferably the container 18 is tubular in shape and is formed of spirally wound paper layers which are biodegradable. The container 18 also preferably has a predetermined interior length substantially the same as the disposable applicators 20 to prevent undesired lengthwise movement of the applicators within the container 18. For a similar purpose, the interior diameter of the container 18 is also preferably substantially equal to the diameter of the predetermined number of applicators when grouped together. In the illustrated embodiment showing seven disposable applicators 20, the interior cross-sectional diameter of the container 18 is preferably substantially equal to three times the diameter of the applicators to form the compacted nested arrangement as shown in the illustrated embodiment of FIG. 1.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A disposable applicator for facilitating the injection of a desired dosage of a gel-like medicine into a body cavity after the application is filled with the desired dosage of the medicine, said disposable applicator comprising:

a barrel having a tubular shape and comprising a plurality of spirally wound paper layers, said barrel having opposing first and second open ends, the first open end of said barrel for permitting the passage of a gel-like medicine therethrough to fill said barrel and for being inserted into a body cavity to inject the medicine into the body cavity from the thus filled barrel, the first open end of said barrel having an inturned lip to facilitate insertion into the body cavity;

a plunger slidably positioned within said barrel and movable relative to said barrel between an unfilled position wherein said barrel contains no medicine and a filled position wherein said barrel contains a desired dosage of medicine, said plunger having a tubular shape and comprising a plurality of spirally wound paper layers, said plunger having opposing first and second ends, the first end of said plunger being closed to serve as the working end of the plunger for ejecting the medicine from said barrel as said plunger is moved from the filled position to the unfilled position, the second end of said plunger including inwardly crimped portions to substantially close the second end of said plunger to thereby prevent the inadvertent or accidental filling with medicine of said plunger rather than said barrel, the length of said plunger being greater than the length of said barrel and of such length that said inwardly crimped portions on said second end are always exposed irrespective of the barrel being filled with medicine or unfilled; and indicia means on a predetermined outer surface portion of said plunger for indicating that said barrel contains the desired dosage of medicine when said plunger extends outwardly from the second end of said barrel in the filled position thereby exposing said indicia means.

2. A disposable applicator according to claim 1 wherein said plunger has a circular cross-section and, wherein said inwardly crimped portions of said plunger and portions adjacent thereto are contained within an imaginary circle as defined by said plunger.

3. A disposable applicator according to claim 1 wherein said inwardly crimped portions of said plunger extend lengthwise along a portion of said plunger and define a star pattern in end view.

4. A disposable applicator according to claim 1 wherein said inwardly crimped portions of said plunger extend lengthwise along a portion of said plunger and define a saddle pattern in end view.

5. A disposable applicator according to claim 1 wherein said indicia means comprises ink and wherein said ink is of a type approved for direct human contact.

6. A disposable applicator according to claim 1 wherein said paper layers of said barrel and said plunger are of a type approved for direct human contact.

7. A package for facilitating the injection of a desired number of successive dosages of a gel-like medicine into a body cavity, said package comprising:

a container having a tubular shape with opposing first and second ends, the first end of said container being closed and the second end of said container being open;

a removable closure cap covering the second end of said container; and a predetermined number of disposable applicators positioned within said container corresponding to a number of desired dosages of a medicine, each of said disposable applicators comprising a barrel having a tubular shape and comprising a plurality of spirally wound paper layers, said barrel having opposing first and second open ends, the first open end of said barrel for permitting the passage of a gel-like medicine therethrough to fill said barrel and for being inserted into a body cavity to inject the medicine into the body cavity from the thus filled barrel, the first open end of said barrel having an inturned lip to facilitate insertion into the body cavity;

a plunger slidably positioned within said barrel and movable relative to said barrel between an unfilled position wherein said barrel contains no medicine and a filled position wherein said barrel contains a desired dosage of medicine, said plunger having a tubular shape and comprising a plurality of spirally wound paper layers, said plunger having opposing first and second ends, the first end of said plunger being closed to serve as the working end of the plunger for ejecting the medicine from said barrel as said plunger is moved from the filled position to the unfilled position, the second end of said plunger including inwardly crimped portions to substantially close the second end of said plunger to thereby prevent the inadvertent or accidental filling with medicine of said plunger rather than said barrel, the length of said plunger being greater than the length of said barrel and of such length that said inwardly crimped portions on said second end are always exposed irrespective of the barrel being unfilled or filled with medicine; and indicia means on a predetermined outer surface portion of said plunger for indicating that said barrel contains the desired dosage of medicine when said plunger extends outwardly from the second end of said barrel in the filled position thereby exposing said indicia means.

8. A package according to claim 7 wherein said container comprises a plurality of spirally wound paper layers.

9. A package according to claim 7 wherein each of said disposable applicators has a predetermined length substantially equal to an interior length of said container so that said disposable applicators are positioned within said container so as to prevent undesired lengthwise movement of said applicators within said container.

10. A package according to claim 7 wherein the predetermined number of disposable applicators is seven, and wherein said container has a circular interior cross-section with a diameter substantially equal to three times a diameter of said disposable applicators so that said seven disposable applicators are positioned within said container to prevent undesired radial movement of said applicators within said container.

11. A package according to claim 7 wherein each of said plungers has a circular cross-section, and wherein said inwardly crimped portions of each plunger and portions adjacent thereto are contained within an imaginary circle as defined by said plunger.

12. A package according to claim 7 wherein said inwardly crimped portions of said plunger extend lengthwise along a portion of each plunger and define a star pattern in end view.

13. A package according to claim 7 wherein said inwardly crimped portions of said plunger extend lengthwise along a portion of each plunger and define a saddle pattern in end view.

14. A package according to claim 7 wherein said indicia means on each of said plungers comprises ink, and wherein said ink is of a type approved for direct human contact.

15. A package according to claim 7 wherein said paper layers of said barrel and said plunger of each disposable applicator are of a type approved for direct human contact.

* * * * *